United States Patent
Vadasz et al.

(10) Patent No.: US 10,568,932 B2
(45) Date of Patent: Feb. 25, 2020

(54) SEMAPHORIN 3A FOR TREATMENT AND ASSESSMENT OF SEVERITY OF ASTHMA

(71) Applicant: Medical Research & Development Fund for Health Services Bnai Zion Medical Center, Haifa (IL)

(72) Inventors: Zahava Vadasz, Haifa (IL); Elias Toubi, Haifa (IL)

(73) Assignee: MEDICAL RESEARCH & DEVELOPMENT FUND FOR HEALTH SERVICES BNAI ZION MEDICAL CENTER, Haifa (IL)

(*) Notice: Subject to any disclaimer, the term of this patent is extended or adjusted under 35 U.S.C. 154(b) by 64 days.

(21) Appl. No.: 14/612,326

(22) Filed: Feb. 3, 2015

(65) Prior Publication Data
US 2015/0216929 A1   Aug. 6, 2015

Related U.S. Application Data

(60) Provisional application No. 61/935,346, filed on Feb. 4, 2014.

(51) Int. Cl.
| | | |
|---|---|---|
| A61K 45/06 | (2006.01) | |
| A61K 38/17 | (2006.01) | |
| G01N 33/68 | (2006.01) | |

(52) U.S. Cl.
CPC .......... A61K 38/1709 (2013.01); A61K 45/06 (2013.01); G01N 33/6893 (2013.01); *G01N 2333/4704* (2013.01); *G01N 2800/122* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2009/0324615 A1 | 12/2009 | Ting | |
| 2012/0251539 A1* | 10/2012 | Ting | ............ C07K 16/28 424/134.1 |

FOREIGN PATENT DOCUMENTS

| | | | |
|---|---|---|---|
| WO | WO 2012/131477 | * | 10/2012 |
| WO | 2014/199364 | | 12/2014 |

OTHER PUBLICATIONS

Barnes et al, How Do Corticosteroids Work in Asthma?, Ann Intern Med. 2003;139:359-370.*
De Groot et al, Immunogenicity of protein therapeutics, (Trends Immunol. Nov. 2007;28(11):482-90).*
Sawaki et al., (2011) Intranasal administration of semaphorin-3A alleviates sneezing and nasal rubbing in a murine model of allergic rhinitis. J Pharmacol Sci 117(1): 34-44.
Bombardier et al., (1992) Derivation of the SLEDAI. A disease activity index for lupus patients. The Committee on Prognosis Studies in SLE. Arthritis Rheum 35(6): 630-40.
Caruthers et al., (1987) Chemical synthesis of deoxyoligonucleotides by the phosphoramidite method. Methods Enzymol 154: 287-313.
Catalano (2010) The neuroimmune semaphorin-3A reduces inflammation and progression of experimental autoimmune arthritis. J Immunol 185(10): 6373-83.
Catalano et al., (2006) Semaphorin-3A is expressed by tumor cells and alters T-cell signal transduction and function. Blood 107(8): 3321-9.
Eixarch et al., (2013) Semaphorins 3A and 7A: potential immune and neuroregenerative targets in multiple sclerosis. Trends Mol Med 19(3): 157-64.
Hart et al., (2007) Quantitative and functional impairment of pulmonary CD4+CD25hi regulatory T cells in pediatric asthma. J Allergy Clin Immunol 119(5): 1258-66.
Ji et al., (2009) Expression and function of semaphorin 3A and its receptors in human monocyte-derived macrophages. Hum Immunol 70(4): 211-7.
Karagiannidis et al., (2004) Glucocorticoids upregulate FOXP3 expression and regulatory T cells in asthma. J Allergy Clin Immunol 114(6): 1425-33.
Kigel et al., (2008) Successful inhibition of tumor development by specific class-3 semaphorins is associated with of expression of appropriate semaphorin receptors by tumor cells. PLoS One 3(9): e3287.
Kikutani et al., (2007) Immune semaphorins: increasing members and their diverse roles. Adv Immunol 93: 121-43.
Kou et al., (2012) Decreased expression of semaphorin-3A, a neurite-collapsing factor, is associated with itch in psoriatic skin. Acta Derm Venereol 92(5): 521-8.
Langier et al., (2012) Regulatory T cells in allergic asthma. Isr Med Assoc J 14(3): 180-3.
Larché (2007) Regulatory T cells in allergy and asthma. Chest 132(3): 1007-14.
Lepelletier et al., (2006) Immunosuppressive role of semaphorin-3A on T cell proliferation is mediated by inhibition of actin cytoskeleton reorganization. Eur J Immunol 36(7): 1782-93.
Levings et al., (2001) Human cd25(+)cd4(+) t regulatory cells suppress naive and memory T cell proliferation and can be expanded in vitro without loss of function. J Exp Med 193(11): 1295-302.
Liu et al., (2004) Decreased CD4+CD25+ T cells in peripheral blood of patients with systemic lupus erythematosus. Scand J Immunol 59(2): 198-202.
Nkyimbeng-Takwi et al., (2012) Neuroimmune semaphorin 4A downregulates the severity of allergic response. Mucosal Immunol 5(4): 409-19.
Robinson (2009) Regulatory T cells and asthma. Clin Exp Allergy 39(9): 1314-23.

(Continued)

*Primary Examiner* — Sergio Coffa
(74) *Attorney, Agent, or Firm* — J.A. Lindeman & Co., PLLC

(57) ABSTRACT

The present invention relates to methods of treating Asthma using Semaphorin 3A. The invention further relates to assessing Asthma severity or treatment efficacy, comprising determining Semaphorin 3A level in a biological sample of a subject afflicted with Asthma.

7 Claims, 5 Drawing Sheets

Specification includes a Sequence Listing.

(56) References Cited

OTHER PUBLICATIONS

Sakaguchi et al., (1985) Organ-specific autoimmune diseases induced in mice by elimination of T cell subset. I. Evidence for the active participation of T cells in natural self-tolerance; deficit of a T cell subset as a possible cause of autoimmune disease. J Exp Med 161(1): 72-87.

Sarris et al., (2008) Neuropilin-1 expression on regulatory T cells enhances their interactions with dendritic cells during antigen recognition. Immunity 28(3): 402-13.

Smith et al., (2011) Expression of neuroimmune semaphorins 4A and 4D and their receptors in the lung is enhanced by allergen and vascular endothelial growth factor. BMC Immunol 12: 30.

Takamatsu et al., (2010) Semaphorins guide the entry of dendritic cells into the lymphatics by activating myosin II. Nat Immunol 11(7): 594-600.

Toubi "Semaphorin 3A: A key player in regulation asthma". In: Allergy, Asthma and Immunophysiology: from Basic Science to Clinical Management. Proccedings of the VI World Asthma, Allergy and COPD Forum and XVIII International Congress on Immunorehabilitation and Rehabilitation in Medicine, London (UK), Apr. 27-30, 2013. Edited by Prof. Revaz Sepiashvili. MEDIMOND International Proceedings, Bologna, Italy. pp. 3-5.

Vadasz and Toubi (2012) Semaphorin 3A—a marker for disease activity and a potential putative disease-modifying treatment in systemic lupus erythematosus. Lupus 21(12): 1266-70.

Vadasz and Toubi (2014) Semaphorins: their dual role in regulating immune-mediated diseases. Clin Rev Allergy Immunol 47(1): 17-25.

Vadasz et al., (2010) Neuropilins and semaphorins—from angiogenesis to autoimmunity. Autoimmun Rev 9(12): 825-9.

Vadasz et al., (2011) The involvement of immune semaphorins and neuropilin-1 in lupus nephritis. Lupus 20(14): 1466-73.

Vadasz et al., (2011) The involvement of Neuropilin-1 and immune Semaphorin's in lupus nephritis. Ann Rheum Dis 70 (suppl 2): A47.

Vadasz et al., (2012) Semaphorin 3A is a marker for disease activity and a potential immunoregulator in systemic lupus erythematosus. Arthritis Res Ther 14(3): R146.

Xystrakis et al., (2007) Regulatory T cell therapy as individualized medicine for asthma and allergy. Curr Opin Allergy Clin Immunol 7(6): 535-41.

Yazdani and Terman (2006) The semaphorins. Genome Biol 7(3): 211.

Yeganeh et al., (2013) Emerging mediators of airway smooth muscle dysfunction in asthma. Pulm Pharmacol Ther 26 (1): 105-11.

* cited by examiner

SEMAPHORIN 3A FOR TREATMENT AND ASSESSMENT OF SEVERITY OF ASTHMA

FIELD OF THE INVENTION

The present invention relates to Semaphorin 3A and uses thereof for treatment of Asthma. The invention further relates to assessing Asthma severity and/or treatment efficacy, comprising determining Semaphorin 3A levels in a biological sample of a subject afflicted with Asthma.

BACKGROUND OF THE INVENTION

Asthma is a major public health problem in particular in western countries. For example, in United States nearly 17 million Americans suffer from this disease. In the last two decades Asthma morbidity and mortality have been rising. The most common treatment of Asthma is inhaled corticosteroids which greatly reduce the symptoms of the disease. However, treatment with corticosteroids has been reported markedly to produce systemic side effects. Specifically, adrenal suppression, decreased bone metabolism, and decreased growth are of great concern when it comes to administration of corticosteroids by children. Corticosteroids also produce overall immune suppression, which results in increased susceptibility to infections. In addition, recent studies indicate that continuous daily treatment with corticosteroids had no long-term therapeutic benefit in terms of lung function because although anti-inflammatory therapy reduced the incidence of asthma symptoms in subjects with persistent asthma, it did not alter progressive lung changes or prevent recurrence of symptoms shortly after discontinuation of therapy. Alternative therapeutic approaches include leukotriene inhibitors and anti-IgE. However, those alternative medications have shown only marginal benefits.

Semaphorins are a family of membrane bound and soluble proteins classified into eight sub-classes based on their structural domains. Semaphorins mainly regulate focal adhesion assembly/disassembly and induce cytoskeletal remodeling, thus affecting cell shape, cell attachment to the extracellular matrix, cell motility, and cell migration. Although Semaphorins were originally identified as affecting axon guidance during development of the nervous system, they are now thought to fulfill diverse physiological roles including organogenesis, vascularization, angiogenesis, neuronal apoptosis, and neoplastic transformation. Additionally, recent studies pointed to the involvement of Neuropilin-1 (a receptor for Semaphorin 3) and certain Semaphorins in the regulation of the immune system, and thus these Semaphorins are denoted "immune Semaphorins".

The seven class-3 Semaphorins (Semaphorin 3s), designated by the letters A-G, are the only 5vertebrate secreted Semaphorins. Neuropilins (Nrps) and the type A/D family Plexins (Plexin-A1, -A2, and -A3, and Plexin-D1) act as receptors for Semaphorin 3. Each Semaphorin 3 family member shows distinct binding preference for Nrps. Each Sema3-Nrp complex associates with specific plexins to mediate downstream signaling. Most membrane-bound vertebrate Semaphorins directly bind plexins, while class-3 Semaphorins require Neuropilins as obligate co-receptors.

Semaphorin 3A (Sema3A), a class-3 secreted member of the Semaphorin family, has been established as an axonal guidance factor during development. Interestingly, several lines of evidence suggest that Sema3A also affects immune cell functions. Sema3A has been shown to be expressed by activated T cells and inhibit T cell proliferation and cytokine secretion (Catalano, A et al, 2006, Blood 107: 3321-3329; Lepelletier, Y. et al., 2006, Eur. J. Immunol. 36: 1782-1793). Moreover, the expression of Sema3A, Neuropilin 1 (NP-1), Neuropilin 2 (NP-2), and Plexins was found to be increased on differentiating macrophages and on activated T cells (Ji J D et al., 2009, Human Immunol., 70(4): 211-7). Additionally, Neuropilin-1 expression on regulatory T cells has been shown to enhance interactions with immature dendritic cells (DCs) during antigen recognition, resulting in higher sensitivity to limiting amounts of antigen.

One study has shown that overexpression of Sema3A in a mouse model of collagen-induced arthritis resulted in reduced incidence, disease severity, and articular inflammation. Moreover, in line with results in arthritic mice, the study showed a defective Sema3A expression in $CD4^+$ T cells derived from patients with rheumatoid arthritis (Catalano A. et al., 2010, J. Immunol., 185: 6373-83).

In another study, kidney biopsies from lupus glomerulonephritis (LGN) patients showed stronger staining with anti-NP-1, anti-Semaphorin 3A and anti-Semaphorin 4A antibodies as compared with either normal biopsies or biopsies from patients with primary nephropathy and proteinuria (Vadasz Z. et al., 2011, Lupus, 20:1466-1473). A subsequent study has shown that Sema 3A serum levels in Systemic Lupus Erythematosus (SLE) patients are significantly lower than in healthy individuals (Vadasz Z. et al, 2012, Arthritis Research & Therapy, 14:R146).

International patent application, publication No. WO2014/199364 to the inventors of the present invention, relates to Semaphorin 3A and use thereof in treatment and prognosis of Systemic Lupus Erythematosus (SLE).

U.S. Application Publication No. 2012/0251539 discloses a method of treating an immune-related disorder in a subject, comprising administering to the subject an effective amount of a Sema3A inhibitor, resulting in reduced Sema3A activity in the subject.

In yet another study, it has been shown that administration of Sema3A alleviates sneezing and nasal rubbing in a murine model of Allergic Rhinitis (Sawaki H. et al., 2011, J. Pharmacol. Sci., 117(1): 34-44).

There is an unmet need in the art, for safe and effective approaches to treat asthma. There is also a need for reliable and accurate biomarkers with which treatment efficacy and disease condition and/or severity can be assessed.

SUMMARY OF THE INVENTION

The present invention provides methods and compositions for treatment of Asthma, said methods comprising administration of a pharmaceutical composition comprising Semaphorin 3A or a derivative thereof to a subject afflicted with Asthma. Further provided are methods for determining efficacy of a treatment of Asthma and methods for assessing Asthma condition or severity in a subject.

The present invention is based, in part, on the unexpected finding that Semaphorin 3A serum concentration is inversely correlated to Asthma disease severity. It has been found that Asthma patients express lower levels of Semaphorin 3A on T regulatory cells compared to healthy subjects. Further, the expression of Foxp3, a prominent regulator in the development and function of T regulatory cells, was increased following exposure of T regulatory cells isolated from Asthma patients to Semaphorin 3A.

Without being bound by any theory or mechanism of action, Semaphorin 3A affects T regulatory cells, inter alia, by increasing Foxp3 expression, thereby improving the functionality of these cells in controlling inflammation in Asthmatic patients.

Thus, in some embodiments, the present invention discloses that Semaphorin 3A possesses a prominent role in modulating Asthma. Accordingly, this Semaphorin 3A may be utilized to treat Asthma and/or diagnose an Asthma condition, severity thereof, or progression thereof. In addition, Semaphorin 3A may be utilized as a biomarker for treatment follow-up.

According to one aspect, the present invention provides a method for treating Asthma, said method comprising administering to a subject in need thereof a pharmaceutical composition comprising a therapeutically effective amount of Semaphorin 3A or a derivative thereof.

According to some embodiments, the Semaphorin 3A is selected from a protein, a polypeptide and a peptide. According to some embodiments, the Semaphorin 3A has a sequence as set forth in SEQ ID NO: 1. According to some embodiments, the Semaphorin 3A is an isolated Semaphorin 3A.

According to some embodiments, the subject in need thereof is a subject afflicted with Asthma.

According to some embodiments, the method further comprises administering to said subject an additional treatment for Asthma. According to some embodiments, the additional treatment may include an active agent and may be selected from the group consisting of: corticosteroids, controller medications, mast cell stabilizers and leukotriene modifier. The additional treatment may be administered before, after or concomitantly with the treatment with Semaphorin 3A.

According to some embodiments, the administering is via a route selected from the group consisting of: intravenous, intra-arterial, subcutaneous, intranasal, intra-peritoneal, and by inhalation.

According to some embodiments, the pharmaceutical composition further comprises an additional treatment for Asthma, such as, for example, one or more active agent.

According to another aspect, the present invention provides a method for assessing asthma severity in a subject in need thereof, the method comprising:
a) making a first measurement of Semaphorin 3A levels in a biological sample of the subject;
b) making a second measurement of Semaphorin 3A levels in a second biological sample of the subject; wherein said second measurement is conducted at a later time point than the first measurement; and
c) comparing the first measurement and the second measurement;
wherein an increase in Semaphorin 3A levels from the first to the second measurement is indicative of a decrease in disease severity; and wherein a decrease in Semaphorin 3A levels from the first to the second measurement is indicative of an increase in disease severity.

According to yet another aspect, the present invention provides a method of determining efficacy of a treatment for asthma in a subject, the method comprising:
a) making a first measurement of Semaphorin 3A levels in a first biological sample of said subject;
b) administering to the subject a treatment for Asthma;
c) making a second measurement of Semaphorin 3A levels in a subsequent biological sample of said subject; and
d) comparing the levels of Semaphorin 3A in said first and second biological samples,
wherein an increase in Semaphorin 3A levels from the first to the second biological sample is indicative of said treatment being efficacious.

According to some embodiments, the biological sample is a liquid or a fluid sample. According to some embodiments, the liquid sample is a blood sample. According to some embodiments, the blood sample is processed to produce serum, and the measurements of Semaphorin 3A are determined in the serum. According to some embodiments, the biological sample is serum and the method further comprises diluting the sample. According to some embodiments, the Semaphorin 3A levels is concentration of Semaphorin 3A in the serum.

According to some embodiments, the measurements of Semaphorin 3A are determined in T regulatory cells present in the blood sample.

According to some embodiments, the Semaphorin 3A levels is percentage of T regulatory cells that express Semaphorin 3A.

According to some embodiments, the T regulatory cells express at least one of: CD4 and CD25.

According to some embodiments, the increase in Semaphorin 3A levels is by at least 1.5 fold. According to some embodiments, the increase in Semaphorin 3A concentration is by at least 1.5 fold. According to some embodiments, the increase in Semaphorin 3A expression on T regulatory cells is by at least 1.2 fold.

According to some embodiments, the treatment for Asthma is selected from the group consisting of: Semaphorin 3A, corticosteroids, controller medications, mast cell stabilizers and leukotriene modifier.

According to some embodiments, the second measurement is performed during or after the treatment.

According to some embodiments, the asthma severity is selected from: intermittent, mild, moderate and severe.

According to yet another aspect, the present invention provides a kit for monitoring asthma severity in a subject, comprising means for making a first and a second measurement of semaphorin3A levels in a biological sample of a subject and instructions for using said kit, wherein an increase in Semaphorin 3A levels from the first to the second measurement is indicative of a decrease in disease asthma severity; and wherein a decrease in Semaphorin 3A levels from the first to the second measurement is indicative of an increase in disease severity.

According to yet another aspect, the present invention provides a kit for determining efficacy of a treatment for asthma in a subject in need thereof, comprising means for making a first and a second measurement of semaphorin3A levels in a biological sample of a subject and instructions for using said kit, wherein an increase in Semaphorin 3A expression from the first to the second measurement is indicative of said treatment being efficacious.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
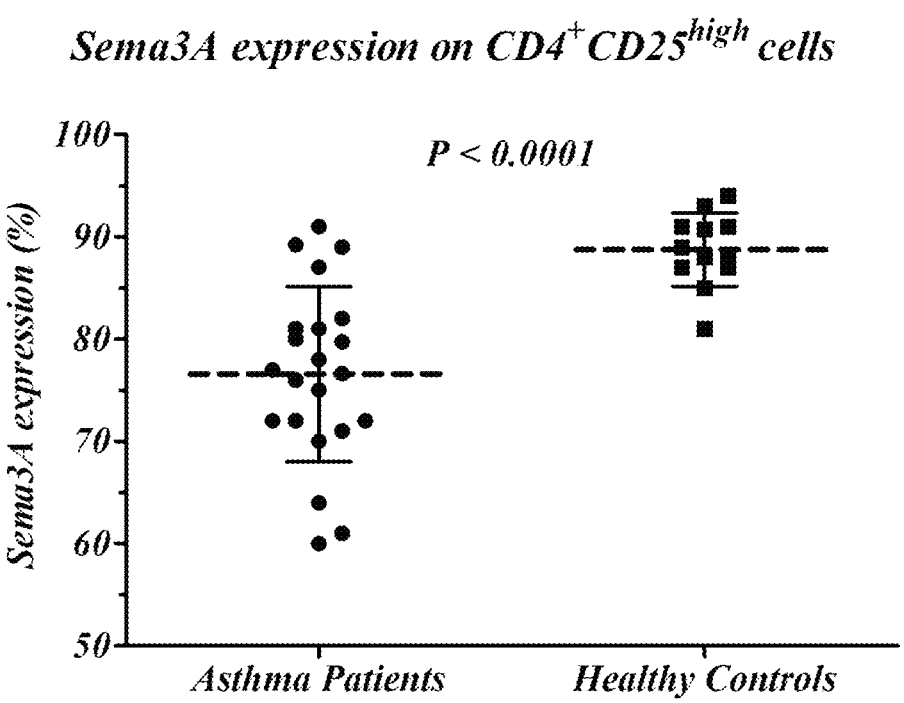
FIG. 1 is a dot plot demonstrating Semaphorin 3A expression on T regulatory cells (CD4+\CD25+) in asthma patients and in healthy subjects (control). Results are presented as percentages of T regulatory cells (CD4+\CD25+) expressing Semaphorin 3A.

The present invention provides, according to one aspect, a method for treating Asthma, the method comprising administering to a subject in need thereof a pharmaceutical composition comprising a therapeutically effective amount of Semaphorin 3A or a derivative thereof. According to a further aspect, the present invention provides methods of monitoring Asthma, based on the levels of Semaphorin 3A in a sample of a subject. According to some embodiments, the levels of Semaphorin 3A are concentration of this protein in the serum or expression on T regulatory cells. According to yet a further aspect, the present invention provides a method of determining the efficacy of a treatment to Asthma, based on assessing and comparing the serum concentration or expression on T regulatory cells of Semaphorin 3A in various time points.

Asthma is a chronic inflammatory disease involving many different cell types and cellular processes. Several lines of evidence suggest that in the long term this inflammation leads to remodeling of the airways, airflow obstruction, and bronchial hyperreactivity, and is present even in patients with intermittent disease. Regulatory T cells (Tregs) are a subpopulation of T cells which modulate inflammation by regulating the immune system.

Asthma is typically assessed by physical examination, medical history, and spirometry. Evidence shows that some of the asthmatic patients are either undiagnosed or misdiagnosed. Further, the known methods of assessing asthma are qualitative rather than being quantitative providing inaccurate assessment of disease condition.

The present invention is advantageous over the current asthma determination by clinical observation, in that it provides quantitative and accurate assessment of asthma thus enables monitoring the severity and/or progression of the disease. Such accurate method facilitates the appropriate use of medications that can improve symptom control, lung function, and quality of life in patients.

It is to be understood that Semaphorin 3A is interchangeable with any alternative name or synonym of this protein known in the art. Typical semaphorin-3A synonyms include, but are not limited to, collapsin 1, semaphorin III and Sema 3A.

As used herein the term "T regulatory cells" is interchangeable with the terms "Treg", "regulatory T cells" and "suppressor T cells". T regulatory cells refer to a subpopulation of T cells which modulate the immune system, maintain tolerance to self-antigens, and abrogate autoimmune disease. Those Treg cells can either be naturally occurring or induced by the conversion of naive T cells in the presence of TGF-beta. Regulatory T cells may be detected by markers. The most well-understood and known Treg cells are those that express CD4 (CD4+) and CD25 (CD25+). Foxp3 can be used as a marker for mouse and human CD4+CD25+ T cells, although recent studies have also shown evidence for Foxp3 expression in CD4+CD25− T cells. Foxp3 is a prominent regulator of T cells known to possess suppressive effect on TH1 and TH2 cells and thereby to inhibit inflammation. An additional Treg population includes cells expressing Tr1, Th3, CD8+CD28+, and Qa-1. The contribution of this population to self-tolerance and immune homeostasis is less well defined.

The present invention is based, in part, on the unexpected finding that Sema3A expression on Treg cells is higher in healthy subjects. Thus, according to embodiments of the present invention, the therapeutic effect of Sema3A in asthmatic patients is mediated by Treg cells. The present invention is further partially based on the finding that Semaphorin 3A serum concentration is inversely correlated to Asthma disease severity. According to embodiments of the present invention, the semaphorin 3A that appear in the serum originate from Treg cells that secret this protein.

As presented herein below, the expression of Semaphorin 3A on Treg cells of healthy subjects is significantly higher than on Treg cells of Asthmatic patients. Further, the concentration of Semaphorin 3A in the serum is inversely correlated to asthma severity. Namely, Semaphorin 3A concentration in serum of healthy subjects is higher than in mild to moderate asthma patients and is higher in mild to moderate subjects as compared to severe asthma patients. It was further shown that Semaphorin 3A increases Foxp3 expression on Treg cells. In view of the above and without being bound by any theory or mechanism of action, Semaphorin 3A is an immune-regulator in asthma and has a regulatory effect on Tregs.

According to one aspect, the present invention provides a method for treating Asthma, the method comprising administering to a subject in need thereof a pharmaceutical composition comprising a therapeutically effective amount of Semaphorin 3A or a derivative thereof.

As used herein, the term "treating" includes, but is not limited to, any one or more of the following: abrogating, ameliorating, inhibiting, attenuating, blocking, suppressing, reducing, delaying, halting, alleviating or preventing symptoms associated with Asthma, and/or Asthma related pathology and condition. Each possibility represents a separate embodiment of the present invention.

According to some embodiments, by denoting Asthma it is meant to include asthma caused by genetic, environmental factors or a combination thereof. According to some embodiments, the asthma is occupational asthma.

Symptoms of Asthma include, but are not limited to, one or more of the symptoms selected from the group consisting of: wheezing, shortness of breath, chest tightness, coughing, and appearance of sputum. Each possibility represents a separate embodiment of the present invention. Symptoms are usually worse at night and in the early morning or in response to exercise. It is to be noted that some people with asthma rarely experience symptoms, usually in response to triggers, whereas others may have marked and persistent symptoms. Accordingly, the methods of the present invention encompass patients that have marked and persistent symptoms as well as patients that rarely experience symptoms. According to some embodiments, treating Asthma refers to ameliorating and/or preventing at least one of the symptoms caused by Asthma. According to some embodiments, systemic symptoms comprise symptoms selected from the group consisting of: systemic malaise, fatigue, fever and a combination thereof. Each possibility represents a separate embodiment of the present invention.

According to some embodiments, a subject in need thereof is a subject afflicted with Asthma or with a disorder associated with Asthma. According to some embodiments, the subject is symptomatic. According to some embodiments, the subject is asymptomatic. As used herein. The term "subject" is interchangeable with the term "patient" or "individual". The subject may be a human subject. Alternatively, the subject may be a mammal. The subject may be a subject who has been diagnosed with or is predisposed to Asthma. A subject may also be referred to being "at risk of suffering" from Asthma. This subject has not yet developed characteristic disease pathology, however is known to be predisposed to the disease due to family history, being genetically predispose to developing Asthma, or diagnosed with a disease or disorder that predisposes them to developing Asthma.

According to some embodiments, a therapeutically effective amount refers to an amount sufficient to induce a decrease in Asthma disease activity. According to some embodiments, a therapeutically effective amount refers to an amount sufficient to increase measurement of Semaphorin 3A serum concentration in a sample of a subject to be at least 450 ng/ml. According to some embodiments, a therapeutically effective amount refers to an amount sufficient to increase the percentage of Treg cells expressing Semaphorin 3A in a biological sample of a subject to be at least 90% of the Treg cells. According to some embodiments, a therapeutically effective amount refers to an amount sufficient to ameliorate and/or prevent at least one of the symptoms associated with Asthma.

According to some embodiments, Semaphorin 3A or its derivative is from a mammalian origin. According to some embodiments, Semaphorin 3A is an isolated Semaphorin 3A. According to some embodiments, Semaphorin 3A or its derivative is from a human origin. According to some embodiments, Semaphorin 3A as used herein is a human Semaphorin 3A having an amino-acid sequence as set forth in SEQ ID NO: 1. The polynucleotide sequence as set forth in SEQ ID NO: 2 corresponds to the cDNA encoding human Semaphorin 3A as set forth in SEQ ID NO: 1.

According to some embodiments, Semaphorin 3A or its derivative is a recombinant protein, polypeptide or peptide.

As used herein the term "derivative thereof" encompasses any form of naturally occurring semaphorin 3A and includes splice variants of semaphorin 3A, or mutant forms of semaphorin 3A. Mutant forms of semaphorin 3A include truncated, or point mutated forms of semaphorin 3A.

According to some embodiments, Semaphorin 3A derivative may be a fragment or an analogue of a naturally occurring Semaphorin 3A that exhibits substantial identical functionality to the naturally occurring Semaphorin 3A. According to some embodiments, Semaphorin 3A derivative refers to a polypeptide having at least 70%, at least 80% or at least 90% homology to the naturally occurring Semaphorin 3A. Each possibility represents a separate embodiment of the invention. According to some embodiments, homology is interchangeable with identity.

According to some embodiments, Semaphorin 3A further comprises a protein tag. According to some embodiments, Semaphorin 3A comprises a protein tag upon production but the tag is cleaved and/or removed from Semaphorin 3A prior to incorporation into the composition of the invention. Cleavage and/or removal of a tag may be performed by any method known in the art, such as, but not limited to, enzymatic and/or chemical cleaving, so long Semaphorin 3A remains functional. According to some embodiments, functional Semaphorin3A refers to Semaphorin 3A which is able to reduce Asthma activity and/or ameliorate at least one of Asthma symptoms. Each possibility represents a separate embodiment of the present invention.

As used herein, the term "protein tag" refers to a peptide sequence bound to the N-terminus or C-terminus of a protein. According to some embodiments, a protein tag may comprise a glycoprotein. According to some embodiments, a protein tag may be used for separation and/or purification of the bound protein. Each possibility represents a separate embodiment of the present invention. Non-limiting examples of protein tags are: Myc, Human influenza hemaglutinin (HA), Flag, His, Gluthathione-S-Transferase (GST) and a combination thereof. Each possibility represents a separate embodiment of the present invention.

As used herein, the term "isolated" means either: 1) separated from at least some of the components with which it is usually associated in nature; 2) prepared or purified by a process that involves the hand of man; and/or 3) not occurring in nature.

According to some embodiments, isolated Semaphorin 3A as disclosed herein may be produced by recombinant or chemical synthetic methods. According to some embodiments, Semaphorin 3A as disclosed herein may be produced by recombinant methods from genetically-modified host cells. Any host cell known in the art for the production of recombinant proteins may be used for the present invention. According to some embodiments, the host cell is a prokaryotic cell. Representative, non-limiting examples of appropriate prokaryotic hosts include bacterial cells, such as cells of *Escherictahia coli* and *Bacillus subtilis*. According to other embodiments, the host cell is a eukaryotic cell. According to some exemplary embodiments, the host cell is a fungal cell, such as yeast. Representative, non-limiting examples of appropriate yeast cells include *Saccharomyces cerevisiae* and *Pichia pastoris*. According to additional exemplary embodiments, the host cell is a plant cell.

Following are non-limiting examples of recombinant and chemical synthetic methods suitable for production of Semaphorin 3A, according to the present invention.

Recombinant Expression

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the terms "polypeptide" and "protein" are used interchangeably and refer to a polymer of amino acid residues.

As used herein, the term "DNA construct" refers to an artificially assembled or isolated nucleic acid molecule which comprises a gene of interest or a coding region of interest. According to some embodiments, a gene of interest is a gene encoding human Semaphorin 3A. According to some embodiments, a coding region of interest is a coding region encoding Semaphorin 3A. According to some embodiments, a coding region of interest is a coding region encoding for human Semaphorin 3A as set forth in SEQ ID NO:2.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the term "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Semaphorin 3A may be synthesized by expressing a polynucleotide molecule encoding Semaphorin 3A in a host cell, for example, a microorganism cell transformed with the nucleic acid molecule.

DNA sequences encoding wild type polypeptides, such as Semaphorin 3A, may be isolated from any cell producing them, using various methods well known in the art. For example, a DNA encoding the wild-type polypeptide may be amplified from genomic DNA by polymerase chain reaction (PCR) using specific primers, constructed on the basis of the nucleotide sequence of the known wild type sequence.

The genomic DNA may be extracted from the cell prior to the amplification using various methods known in the art.

The isolated polynucleotide encoding the wild type polypeptide may be cloned into any vector known in the art.

Upon isolation and cloning of the polynucleotide encoding the wild type polypeptide, desired mutation(s) may be introduced by modification at one or more base pairs, using methods known in the art, such as for example, site-specific mutagenesis, cassette mutagenesis, recursive ensemble mutagenesis and gene site saturation mutagenesis. Methods are also well known for introducing multiple mutations into a polynucleotide. For example, introduction of two and/or three mutations can be performed using commercially available kits, such as the QuickChange site-directed mutagenesis kit (Stratagene).

An alternative method to producing a polynucleotide with a desired sequence is the use of a synthetic gene. A polynucleotide encoding a desired polypeptide may be prepared synthetically, for example using the phosphoroamidite method (see, Beaucage et al., Curr Protoc Nucleic Acid Chem. 2001 May; Chapter 3: Unit 3.3; Caruthers et al., Methods Enzymol. 1987, 154:287-313).

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

In the case of a fusion protein, or a protein fused with a protein tag, different polynucleotides may be ligated to form one polynucleotide. The polynucleotide encoding the polypeptide of the invention, such as, but not limited to the polynucleotide encoding human Semaphorin 3A (SEQ ID NO:2), may be incorporated into a wide variety of expression vectors, which may be transformed into in a wide variety of host cells.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

Representative, non-limiting examples of appropriate hosts include bacterial cells, such as cells of *E. coli* and *Bacillus subtilis*.

The polypeptides may be expressed in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on betagalactosidase (pEX); maltose binding protein (pMAL); and glutathione S-transferase (pGST).

The polypeptides may be designed to include a protein tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the polypeptide may be identified in cell extracts of the transformed cells. Transformed hosts expressing the polypeptide may be identified by analyzing the proteins expressed by the host, for example, using SDS-PAGE and comparing the gel to an SDS-PAGE gel obtained from the host which was transformed with the same vector but not containing a nucleic acid sequence encoding the desired polypeptide.

The desired polypeptides which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof. The polypeptides of the invention may be produced as fusion proteins, attached to an affinity purification protein tag, such as a His-tag, in order to facilitate their rapid purification.

The isolated polypeptide may be analyzed for its various properties, for example specific activity, using methods known in the art. In a non-limiting example, isolated Semaphorin 3A may be analyzed for its ability to increase expression of Foxp3 on $CD25^+/CD4^+$ Treg cells isolated from Asthma patients.

Conditions for carrying out the aforementioned procedures as well as other useful methods are readily determined by those of ordinary skill in the art.

Semaphorin 3A according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

According to another aspect, the present invention provides a method for assessing asthma severity in a subject in need thereof, the method comprising:
a) obtaining a first biological sample from the subject;
b) making a first measurement of Semaphorin 3A or a derivative thereof levels in the biological sample of the subject;
c) obtaining a second biological sample from the subject;
d) making a second measurement of Semaphorin 3A or a derivative thereof levels in the second biological sample of the subject; wherein said second measurement is conducted at a later time point than the first measurement; and
e) comparing the first measurement and the second measurement;

wherein an increase in Semaphorin 3A or a derivative thereof levels from the first to the second measurement is indicative of a decrease in disease severity; and wherein a decrease in Semaphorin 3A or a derivative thereof levels from the first to the second measurement is indicative of an increase in disease severity.

According to some embodiments, a decrease in Asthma disease activity or severity is characterized by amelioration of at least one of the symptoms of Asthma. According to some embodiments, an increase in Asthma disease activity is characterized by worsening of at least one symptom of Asthma.

As used herein the term "assessing asthma severity" refers to evaluating, determining or classifying asthma condition in a subject. Each possibility represents a separate embodiment of the invention.

Typically, asthma severity may be determined according to the clinical symptoms of the patient. For example, asthma severity may be determined according to lung function tests (spirometry and Peak Expiratory Flow [PEF]). Alternatively, asthma severity may be determined according to the Global Initiative for Asthma (GINA) guidelines. Asthma severity may change over time. In addition, a person in any category can have severe asthma attacks.

In some embodiments, the method provided herein allows, for the first time, a quantitative tool for assessing asthma severity.

As used herein, by the term "quantitative" it is meant to assess asthma severity by assessing the differences in the quantity of expression or levels of sema3A in two separate measurements, as determined by any means, known in the art. According to some embodiments, "quantitative" differences, may be statistically significant, or in some embodiments, when viewed as a whole or over a prolonged period of time, etc., indicate a trend in terms of differences in Semaphorin 3A levels.

According to some embodiments, a statistically significant difference between the level of semaphorin 3A in the first and second samples obtained from the subject provides an indication regarding the asthma severity of the subject or the progression or regression of the disease.

According to some embodiments, asthma severity is selected from the group consisting of: intermittent asthma, mild asthma, moderate asthma and severe asthma. According to some embodiments, asthma severity is selected from the group consisting of: intermittent asthma, mild to moderate asthma and severe asthma. For example, semaphorin 3A serum concentration of below 220 ng/ml or 200 ng/ml is indicative that the asthma is severe. Semaphorin 3A serum concentration of between 230 ng/ml to 400 ng/ml is indicative that the asthma is at the stage of mild to moderate. Semaphorin 3A serum concentration of above 400 ng/ml or 450 ng/ml is indicative that the subject is healthy.

According to some embodiments, the method of assessing asthma severity further comprises classification according to known protocols, including, but not limited to: PEF and GINA. Namely, the method of the invention provides an overall asthma assessment based on both the quantitative measurement of sema3A levels and the qualitative assessment based on the clinical parameters of patients.

According to some embodiments, asthma is considered intermittent if (without treatment) any one or more of the following occurs: symptoms occur less than 2 days a week, attacks do not interfere with daily activities, night time symptoms occur less than 2 days a month, and lung function tests are normal when the person is not having an asthma attack. For example, the lung function tests may show 80% or more of the expected normal value and PEF varies less than 20% from morning to afternoon. According to some embodiments, asthma is considered mild if (without treatment) any one or more of the following occurs: symptoms occur more than 2 days a week but not every day, attacks or symptoms interfere with daily activities, nighttime symptoms occur 3 to 4 times a month, and lung function tests are normal when the person is not having an asthma attack. For example, the lung function tests may show 80% or more of the expected normal value and PEF varies 20% to 30% from morning to afternoon. According to some embodiments, asthma is considered moderate if (without treatment) any one or more of the following occurs: symptoms occur daily, inhaled short-acting asthma medication is used every day, symptoms interfere with daily activities, nighttime symptoms occur more than 1 time a week, but do not happen every day, and lung function tests are abnormal (for example, more than 60% to less than 80% of the expected value and PEF varies more than 30% from morning to afternoon). According to some embodiments, asthma is considered severe if (without treatment) any one or more of the following occurs: symptoms occur throughout each day, severely limit daily physical activities, nighttime symptoms occur often, sometimes every night, and lung function tests are abnormal (60% or less of expected value), and PEF varies more than 30% from morning to afternoon.

According to some embodiments, the term "at a later time point" refers to any time point in between or after 1-24 hours or 1-90 days (such as, for example, 1, 2, 3, 4, 5, 6, 7, 14, 21, 30, 60, or 90 days) from the first measurement. Each possibility represents a separate embodiment of the invention According to some embodiments, treating Asthma is accompanied with an increase in the serum concentration of Semaphorin 3A or an increase in the expression of Semaphorin 3A on Treg cells. According to those embodiments, the present invention provides a method for determining efficacy of a treatment for Asthma in a subject in need thereof, comprising: making a first measurement of Semaphorin 3A concentration in the serum or expression on Treg cells of a subject in need thereof; administering a treatment for Asthma to the subject; making a second measurement of Semaphorin 3A concentration in the serum or expression on Treg cells of a subject; and comparing said first measurement and said second measurement, wherein an increase in Semaphorin 3A serum concentration or expression on Treg cells from the first to the second measurement is indicative of said treatment being efficacious.

The methods for determining efficacy of a treatment according to the present invention are based in part on the unexpected discovery that Semaphorin 3A serum concentration and/or expression on Treg cells in a subject is inversely correlated to Asthma disease activity. According to some embodiments, treatment of Asthma leading to an increase in Semaphorin 3A serum concentration or an increase in the expression of sema 3A on Treg cells in a subject being treated, is an efficacious treatment.

As used herein, the term "Semaphorin 3A levels" refers to Semaphorin 3A mRNA or Semaphorin 3A protein expression level in a biological sample and encompasses measurements of absolute values such as total amount or of arbitrary units. "Arbitrary units" are usually measured in methodologies such as fluorescence spectroscopy, Fluorescence Activated Cells Sorter (FACS), or densitometry of western/northern blotting. The term also encompasses determining in a given cell population the percentage of cells that express Semaphorin 3A. According to one embodiment, Semaphorin 3A expression refers to concentration in a liquid sample. The term "concentration" refers to the abundance of a constituent divided by the total volume of a mixture.

According to some embodiments, "an increase in Semaphorin 3A levels from the first to the second measurement" is an increase by at least 1-5 fold (for example, 1.2, 1.4, 1.5, 1.6, 1.8, 2, 3, 4, or 5 fold). Each possibility represents a separate embodiment of the present invention. According to some embodiments, "an increase in Semaphorin 3A levels from the first to the second measurement" is an increase by at least 10-80% (for example, 10%, at least 20%, at least 30%, at least 40%, at least 50%, at least 60%, at least 70% or at least 80%). Each possibility represents a separate embodiment of the present invention.

According to some embodiments, "a decrease in Semaphorin 3A levels from the first to the second measurement" is a decrease by at least 1.2, 1.4, 1.6, 1.8, 2, 3, 4, or 5 fold. Each possibility represents a separate embodiment of the present invention. According to some embodiments, "a decrease in Semaphorin 3A levels from the first to the second measurement" is a decrease by at least 10%, at least 20%, at least 30%, at least 40%, at least 50%, at least 60%, at least 70% or at least 80%. Each possibility represents a separate embodiment of the present invention.

According to some embodiments, the efficacy of a treatment for Asthma is further indicated by improving, preventing, abrogating, the at least one of the symptoms associated with Asthma, including, but not limited to wheezing, shortness of breath, chest tightness, and coughing, appearance of sputum. Each possibility represents a separate embodiment of the present invention.

According to some embodiments, the first measurement is taken as close as possible prior to the beginning of the Asthma treatment, preferably, for example, within a day of the beginning of treatment. According to some embodiments, the first measurement is taken at the time of diagnosing a subject with Asthma or as close as possible to the time of said diagnosis. Each possibility represents a separate embodiment of the present invention. According to some embodiments, the second measurement is taken following termination of the treatment. According to some embodiments, the second measurement is taken in the course of treatment with the Asthma treatment. According to some embodiments, the second measurement is taken at least 1-90 days (for example, 1, 2, 3, 4, 5, 6, 7, 14, 21, 30, 60, or 90 days) after the beginning of the treatment. Each possibility represents a separate embodiment of the present invention. According to some embodiments, the second measurement is taken at least a week after the beginning of the Asthma treatment. According to some embodiments, the second measurement is taken at least 1-90 days (such as, 1, 2, 3, 4, 5, 6, 7, 14, 21, 30, 60, or 90 days) following termination of the Asthma treatment. Each possibility represents a separate embodiment of the present invention. According to some embodiments, the second measurement is taken at least a week following termination of the Asthma treatment.

It is to be noted that, the increase in Semaphorin 3A serum concentration and/or expression on T regulatory cells following treatment according to the present invention is dependent on the specific physiological parameters of each subject. Therefore, treatment according to the embodiments of the present invention may result in a different increase in Semaphorin 3A concentration in a serum or expression on T regulatory cells of a subject. For example, an increase in serum concentration of Semaphorin 3A or expression on T regulatory cells of about 10% may be accounted as treating according to certain embodiments of the invention.

As used herein the term "biological sample" refers to any sample obtained from the subject being tested. According to some embodiments, the biological sample is selected from: cells, tissue and bodily fluid. Each possibility represents a separate embodiment of the invention. According to some embodiments, the biological sample is a solid or a tissue sample. According to some embodiments, the solid sample or tissue sample is obtained from the lungs. According to some embodiments, the biological sample is a fluid sample. According to some embodiments, the fluid sample may be selected from, but not limited to: whole blood, plasma, serum, a sample obtained by broncoalveolar lavage, or combinations thereof. Each possibility represents a separate embodiment of the invention. According to one embodiment, the fluid sample is a serum sample.

The biological sample may be obtained or collected from the subject in any method known in the art. The sample may be collected from the subject by noninvasive, invasive or minimal invasive means. Each possibility represents a separate embodiment of the invention.

According to some embodiments, the sample may be treated prior to being subjected to measuring sema3A levels. According to some embodiments, the sample is serum and is therefore substantially free of cells or debris of cells.

As used herein the term "serum" refers to the component in blood that does not contain white or red blood cells nor clotting factors. Serum includes all proteins not used in blood clotting (coagulation) and all the electrolytes, antibodies, antigens, hormones, and any exogenous substances (e.g., drugs and microorganisms). Typically, for preparing serum, a whole blood sample collected from a patient is inserted into an appropriate tube. Then the whole blood sample is left at room temperature for at least 15 minutes to allow the blood to clot. The clot is removed by centrifuging (for example at 1,000-2,000×g for 10 minutes). The resulting supernatant is designated serum. According to some embodiments, the clotting procedure is conducted by leaving the blood sample at room temperature for at least 30 minutes, or for an hour. Each possibility represents a separate embodiment of the invention. For obtaining plasma from a whole blood sample, the whole blood collected is inserted to commercially available anticoagulant-treated tube (e.g., EDTA-treated or citrate-treated tube). Cells are removed from plasma by centrifugation (for example at 1,000-2,000×g 10 minutes). Centrifugation for 15 minutes at 2,000×g depletes platelets in the plasma sample. The resulting supernatant is designated plasma. According to some embodiments, the liquid (e.g., serum) sample is diluted prior to analysis of sema3A concentration. According to some embodiments, the sample is diluted 1:5, 1:10, 1:20, or 1:100 using, for example, PBS or saline. Each possibility represents a separate embodiment of the present invention. According to one embodiment, the sample is diluted 1:50. Alternatively, the sample may undergo concentration with a suitable membrane pore cut-off size of, for example, 5,000, 10,000, 30,000 or 50,000 kDa is used. Each possibility represents a separate embodiment of the present invention.

According to additional embodiments, the sample may conveniently be frozen after being collected from the subject or after being subjected to a preparation procedure and thawed before determining the levels of semaphorin 3A ,e.g. by an immunoassay.

According to some embodiments, the sample is selected from the group consisting of formalin-fixed paraffin-embedded (FFPE) tissue, fresh frozen (FF) tissue, and tissue comprised in a solution that preserves nucleic acid or protein molecules. Each possibility represents a separate embodiment of the invention.

It should be noted that a "biological sample obtained from the subject" may also optionally comprise a sample that has not been physically removed from the subject.

According to some embodiments, measurement of serum Semaphorin 3A concentration or expression on T regulatory cells may be performed by any method known in the art. According to some embodiments, Semaphorin 3A can be detected and quantified by any of a number of methods well known to those of skill in the art. These may include, but are not limited to, analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as, but not limited to, fluid or gel precipitin reactions, immunodiffusion (single or double), immunohistochemistry, affinity chromatography, immunoelectrophoresis, radioimmunoassay (RIA), enzyme-linked immunosorbent assay (ELISA), immunofluorescent assay, Western blotting, Fluorescence Activated Cell Sorter (FACS) and the like. Each possibility represents a separate embodiment of the invention. According to one embodiment, measurement of serum Semaphorin 3A is performed using an enzyme-linked immunosorbent assay (ELISA).

According to some embodiments and without wishing to be bound by any theory or mechanism of action, administration of Semaphorin 3A to a subject afflicted with Asthma may result in an increase in the expression of Foxp3 in T regulatory cells of said subject. With respect to those embodiments, the present invention provides a method for increasing Foxp3 expression on T regulatory cells of a subject in need thereof, the method comprising administration of a composition comprising therapeutically effective amount of an isolated Semaphorin 3A or a derivative.

According to some embodiments, the method of treating Asthma may further include administering to the subject an additional treatment for Asthma other than the treatment of the present invention. According to some embodiments, the additional treatment may be provided before, after, or concomitantly with the administration of the pharmaceutical compositions comprising the Semaphorin 3A. According to some embodiments, treating Asthma according to the present invention comprises administration of a pharmaceutical composition comprising isolated Semaphorin 3A and an additional agent. Typical treatments for Asthma include, but are not limited to, corticosteroids, controller medications, mast cell stabilizers and leukotriene modifier medications. Each possibility represents a separate embodiment of the invention. Corticosteroids are effective and commonly used for treating Asthma. The use of these medicines leads to better asthma control with fewer symptoms and flare-ups and less of a need for hospitalization. Corticosteroids may be administrated in inhaled dosage form or administered systemically by oral or intravenous route of administration. Inhaled corticosteroids include, but are not limited to, Beclomethasone (Qvar®), Budesonide (Pulmicort®, Symbicort®), Flunisolide (Aerobid®), Fluticasone (Flovent® HFA, Advair®), Mometasone (Asmanex®) and Triamcinolone (Azmacort®). Systemic steroids include, but are not limited to, Methylprednisolone (Medrol®, Methylpred®, Solu-Medrol®), Prednisone (Deltasone®), Prednisolone (Prelone®, Pediapred®, Orapred®).

Mast cell stabilizers are inhaled asthma medications that work by preventing the release of histamine and other inflammatory substances from mast cells. They effectively prevent asthma symptoms, especially in children with allergies and asthma and in people with exercise-induced asthma. Mast cell stabilizers include for example, but are not limited to, Cromolyn sodium (Intal®).

Leukotrienes are chemicals that occur naturally in mammals body and cause tightening of airway muscles and production of mucus. Leukotriene modifier medications work by blocking the actions of leukotrienes in the body. Leukotriene modifiers include, but are not limited to, Montelukast (Singulair®), Zafirlukast (Accolate®), and Zileuton (Zyflo®).

According to some embodiments, the composition of the invention further comprises a drug selected from the group consisting of: a corticosteroid, a cytotoxic drug, an immunosuppressive drug, an analgesic, immunoglobulins and a combination thereof. Each possibility represents a separate embodiment of the present invention.

According to some embodiments, any suitable route of administration to a subject may be used for the composition of the present invention, including but not limited to, local and systemic routes. Exemplary suitable routes of administration include, but are not limited to: orally, intranasally, parenterally, intravenously, topically, or by inhalation. According to another embodiment, systemic administration of the composition is via an injection. For administration via injection, the composition may be formulated in an aqueous solution, for example in a physiologically compatible buffer including, but not limited, to Hank's solution, Ringer's solution, or physiological salt buffer. Formulations for injection may be presented in unit dosage forms, for example, in ampoules, or in multi-dose containers with, optionally, an added preservative.

According to another embodiment, administration systemically is through a parenteral route. According to some embodiments, parenteral administration is administration intravenously, intra-arterially, intramuscularly, intraperitoneally, intradermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration. The term "topical administration", as used herein, refers to administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present invention include, for example, emulsion, mousse, lotion, solution and serum.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1

Figure 2:
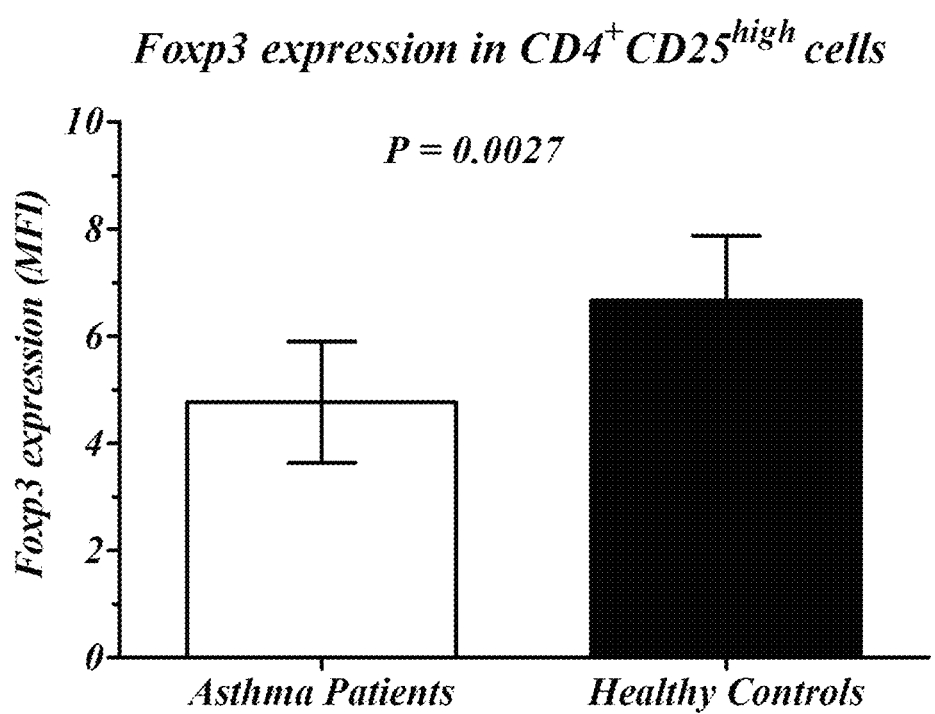
FIG. 2 is a bar graph demonstrating FoxP3 expression on T regulatory cells (CD4+\CD25+) in asthma patients and in healthy subjects (control). Results are presented as Mean Fluorescence Intensity (MFI, arbitrary units).

Lower Semaphorin 3A and Foxp3 Expression in T Regulatory Cells of Asthmatic Patients as Compared to Normal Healthy Subjects Whole blood from healthy subjects (control) and asthmatic patients (active and non-active) was collected. The expression level of Semaphorin 3A and Foxp3 was assessed in T regulatory cells (CD4$^+$\CD25$^+$) using Fluorescent Activated Cell Sorting (FACS). Semaphorin 3A expression on CD4$^+$\CD25$^+$ cells of active asthma patients was significantly lower than of healthy subjects (66% vs. 89%, P<0.0001, FIG. 1). Also, FoxP3 expression in CD4$^+$\CD25$^+$ cells was lower in patients with active asthma than in normal healthy subjects (4.1 MFI vs. 6.5 MFI, P<0.0027, FIG. 2).

Example 2

Semaphorin 3A Induces Expression of Foxp3 in T Regulatory Cells

HEK-293 cells were infected with NSPI-CMV-FLAG lentivirus comprising FLAG-tagged Semaphorin 3A cDNA or with empty NSPI-CMV-FLAG lentivirus, as previously described (Bombardier C. et al., 1992, Arthritis Rheum., 35:630-640). Accordingly, Conditioned Medium (CM) from HEK293 cells infected by NSPI-CMV-FLAG lentivirus with Semaphorin 3A cDNA contained FLAG-tagged Semaphorin 3A, as set forth in SEQ ID NO:3.

Figure 3:
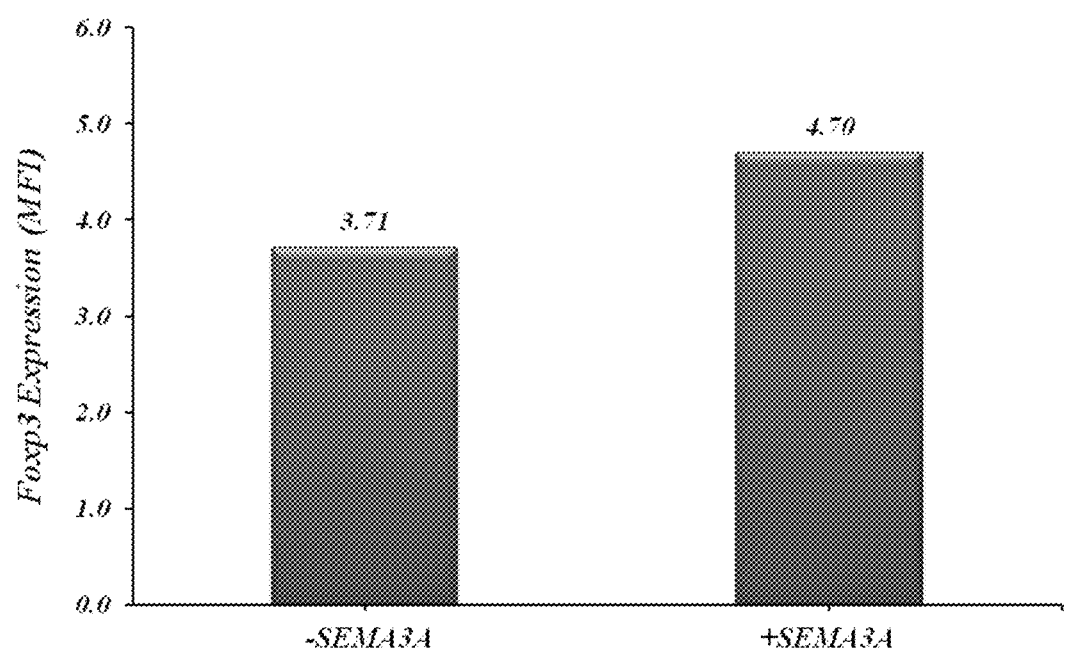
FIG. 3 is a bar graph demonstrating FoxP3 expression on T regulatory cells (CD4+\CD25+) following incubation with HEK-293 conditioned media which either or not contain Semaphorin 3A. Results are presented as Mean Fluorescence Intensity (MFI, arbitrary units).

T regulatory cells were purified from asthmatic patients using magnetic beads. The cells were then incubated with CM of HEK-293 cells containing recombinant human Semaphorin 3A (having SEQ ID NO. 1). T regulatory cells incubated with CM of HEK-293 cells which does not contain Semaphorin 3A were used as control. T regulatory cells were analyzed for the expression of regulatory markers (FoxP3 and CTLA-4) using FACS. As shown in FIG. 3, significant up-regulation of FoxP3 was demonstrated on T regulatory cells incubated with HEK-293 condition medium containing Semaphorin 3A (3.94 MFI in CM without Semaphorin 3A vs. 4.98 MFI in CM with Semaphorin 3A).

Example 3

Figure 4:
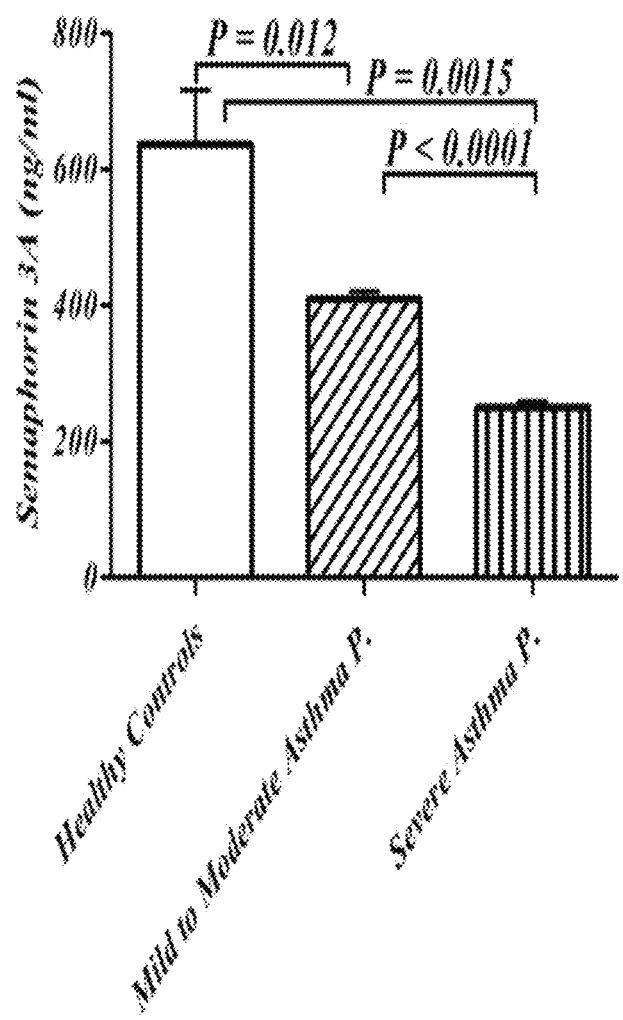
FIG. 4 is a bar graph demonstrating Semaphorin 3A concentrations in the serum of mild-moderate and severe Asthma patients and healthy subjects (control).

Inverse Correlation Between Semaphorin 3A Serum Concentration and Severity of Asthma Serum samples from severe and mild to moderate asthmatic patients and from healthy subjects (control) were collected and subjected to analysis of Semaphorin 3A concentration in serum. The Asthma patients were divided to two groups: mild-moderate and severe, according to the Global Initiative for Asthma (GINA) guidelines. Overall, as shown in FIG. 4, semaphorin 3A inversely correlated to asthma severity, presenting a concentration of about 220 ng/ml, about 400 ng/ml and about 600 ng/ml Semaphorin 3A in sever, mild-moderate and healthy subjects, respectively. The differences between all groups tested were significant.

Example 4

Figure 5:
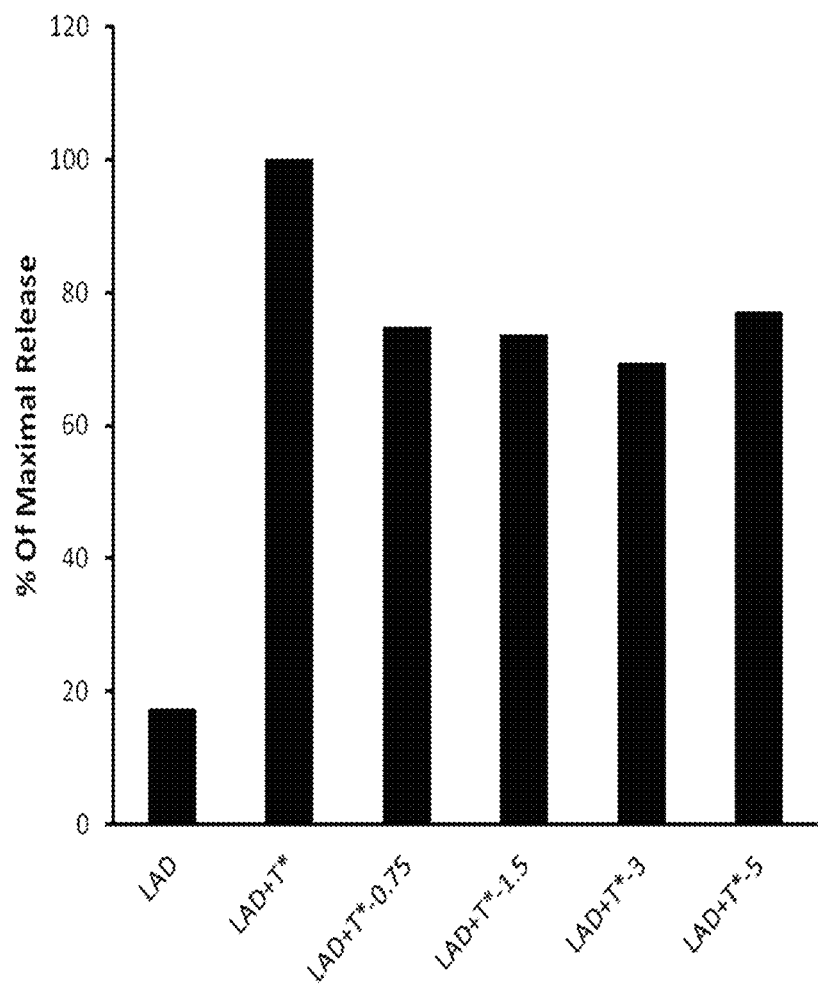
FIG. 5 is a bar graph demonstrating that Semaphorin 3A inhibits degranulation of LAD cells induced by activated T cells membranes (T*).

Semaphorin 3A Inhibits Degranulation of LAD Cells Induced by Activated T Cells Human mast cell line (LAD cells) were incubated at a concentration of $2 \times 10^6$ cells in 4 ml medium (2 ml old medium plus 2 ml fresh medium), over night with stem cell factor 2 (SCF2). The cells were then harvested and $1 \times 10^5$ cells re-were plated in 96 well plate. The cells were incubated over night in 100 µl of medium comprising various concentrations of Semaphorin 3A (0.75 µg\ml, 1.5 µg\ml, or 3 µg\ml) and with activated T cells membranes at a final concentration of 20 µg/ml. Supernatants were then collected and degranulation (β-hexosaminidase release) was evaluated. As can be seen in FIG. 5, activated T cells membranes induce degranulation of the LAD cells. Semaphorin 3A inhibits degranulation induced by the activated T cells membranes in the LAD cells. The results provide further support that Semaphorin 3A acts to attenuate immune cells response medicated by mast cells.

Example 5

In Vivo Studies for Determining Semaphorin 3A Effect in the Ovalbumin (OVA)-induced Asthma Mouse Model In order to assess the effect of Semaphorin 3A on asthma, the Ovalbumin (OVA)-induced asthma mouse model is utilized. This mouse model is widely used to reproduce the airway eosinophilia, pulmonary inflammation and elevated IgE levels found during asthma. Balb/c female mice are induced for OVA sensitization and airway challenge by intraperitoneal injection with 50 µg ovalbumin (OVA; grade V; Sigma-Aldrich) plus 1 mg Alum hydroxide (Sigma-Aldrich) in 200 µl 0.9% sodium chloride (saline; Hospira) every week and until the end of the experiment. Control group is treated identically except that OVA is absent in the solutions. Semaphorin 3A is administered to mice with aerosolized 50 µg recombinant Semaphorin 3A in 50 µl saline 12 hours prior to each administration of OVA by nasal administration or intraperitoneal administration. Mice are euthanized on day 24 and efficiency of sensitization is assessed as changes in airway function after challenge with aerosolized methacholine (Sigma-Aldrich). The effect of Semaphorin 3A on airway hyper-responsiveness is compared to the effect of administration of dexamethasone (3 mg\kg), a synthetic member of the glucocorticoid. Mice are anesthetized, tracheostomized, mechanically ventilated, and lung function is assessed starting from 24 h after the final OVA challenge. The lungs are challenged with increasing doses of aerosolized methacholine using flexiVent™ (Scireq -Scientific Respiratory Equipment). Lung resistance is continuously analyzed and compared between the different treatment groups. In addition, serum total IgE levels and assessment of eosinophilia and total inflammatory cells count is assesses on serum samples. The total IgE and OVA-specific IgE levels is measured in serum samples collected from mice on 16 day is determined using enzyme-linked immunosorbent assay (ELISA) kits (Serotec, Oxford, UK) according to the manufacturer's instructions. The absorbance is measured at 450 nm by a micro plate ELISA reader.

Bronchoalveolar lavage fluid (BALF) is taken from the mice and analyzed. BALF is centrifuged, the supernatant is analyzed for inflammatory cell count including eosinophil, lymphocyte, neutrophil, macrophage and total cells, by using direct microscopic counting with a hemocytometer after exclusion of dead cells by trypan blue staining Th2 cytokines including IL-4 and IL-5 are analyzed in the BALF using an enzyme-linked immunosorbent assay (ELISA) kits (BioSource International, Camarillo, Calif.) according to the manufacturer's protocol.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

The invention claimed is:

1. A method for treating asthma of a subject in need thereof, said method comprising administering systemically to the subject a pharmaceutical composition comprising a therapeutically effective amount of Semaphorin 3A, wherein said effective amount is sufficient to increase measurement of Semaphorin 3A serum concentration in a sample of a subject to be at least 450 ng/ml; thereby treating asthma in said subject.

2. The method of claim 1, wherein said Semaphorin 3A has a sequence as set forth in SEQ ID NO: 1.

3. The method of claim 1, wherein said method further comprises administering to said subject an additional treatment for Asthma.

4. The method of claim 3, wherein said additional treatment is selected from the group consisting of: corticosteroids, controller medications, mast cell stabilizers and leukotriene modifier.

5. The method of claim 1, wherein said administering is via a route selected from the group consisting of: intravenous, intraarterial, subcutaneous, and intraperitoneal.

6. The method of claim 1, wherein said therapeutically effective amount of Semaphorin 3A increases: the levels of Foxp3 expression on T regulatory cells, the percentage of T regulatory cells expressing Semaphorin 3A, and/or Semaphorin 3A concentration in the serum of said subject, when compared to said subject prior treatment with said Semaphorin 3A.

7. The method of claim 6, wherein said increase is by at least 1.2 fold.

* * * * *

SEQUENCE LISTING

<160> NUMBER OF SEQ ID NOS: 3

<210> SEQ ID NO 1
<211> LENGTH: 771
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Gly | Trp | Leu | Thr | Arg | Ile | Val | Cys | Leu | Phe | Trp | Gly | Val | Leu | Leu |
| 1 | | | | 5 | | | | | 10 | | | | | 15 | |
| Thr | Ala | Arg | Ala | Asn | Tyr | Gln | Asn | Gly | Lys | Asn | Asn | Val | Pro | Arg | Leu |
| | | | 20 | | | | | 25 | | | | | 30 | | |
| Lys | Leu | Ser | Tyr | Lys | Glu | Met | Leu | Glu | Ser | Asn | Asn | Val | Ile | Thr | Phe |
| | | | 35 | | | | | 40 | | | | | 45 | | |
| Asn | Gly | Leu | Ala | Asn | Ser | Ser | Ser | Tyr | His | Thr | Phe | Leu | Leu | Asp | Glu |
| | | | 50 | | | | | 55 | | | | | 60 | | |
| Glu | Arg | Ser | Arg | Leu | Tyr | Val | Gly | Ala | Lys | Asp | His | Ile | Phe | Ser | Phe |
| 65 | | | | | 70 | | | | | 75 | | | | | 80 |
| Asp | Leu | Val | Asn | Ile | Lys | Asp | Phe | Gln | Lys | Ile | Val | Trp | Pro | Val | Ser |
| | | | | 85 | | | | | 90 | | | | | 95 | |
| Tyr | Thr | Arg | Arg | Asp | Glu | Cys | Lys | Trp | Ala | Gly | Lys | Asp | Ile | Leu | Lys |
| | | | | 100 | | | | | 105 | | | | | 110 | |
| Glu | Cys | Ala | Asn | Phe | Ile | Lys | Val | Leu | Lys | Ala | Tyr | Asn | Gln | Thr | His |
| | | | | 115 | | | | | 120 | | | | | 125 | |
| Leu | Tyr | Ala | Cys | Gly | Thr | Gly | Ala | Phe | His | Pro | Ile | Cys | Thr | Tyr | Ile |
| | | 130 | | | | | 135 | | | | | 140 | | | |
| Glu | Ile | Gly | His | His | Pro | Glu | Asp | Asn | Ile | Phe | Lys | Leu | Glu | Asn | Ser |
| 145 | | | | | 150 | | | | | 155 | | | | | 160 |
| His | Phe | Glu | Asn | Gly | Arg | Gly | Lys | Ser | Pro | Tyr | Asp | Pro | Lys | Leu | Leu |
| | | | | 165 | | | | | 170 | | | | | 175 | |
| Thr | Ala | Ser | Leu | Leu | Ile | Asp | Gly | Glu | Leu | Tyr | Ser | Gly | Thr | Ala | Ala |
| | | | | 180 | | | | | 185 | | | | | 190 | |
| Asp | Phe | Met | Gly | Arg | Asp | Phe | Ala | Ile | Phe | Arg | Thr | Leu | Gly | His | His |
| | | | | 195 | | | | | 200 | | | | | 205 | |
| His | Pro | Ile | Arg | Thr | Glu | Gln | His | Asp | Ser | Arg | Trp | Leu | Asn | Asp | Pro |
| | | 210 | | | | | 215 | | | | | 220 | | | |
| Lys | Phe | Ile | Ser | Ala | His | Leu | Ile | Ser | Glu | Ser | Asp | Asn | Pro | Glu | Asp |
| 225 | | | | | 230 | | | | | 235 | | | | | 240 |
| Asp | Lys | Val | Tyr | Phe | Phe | Phe | Arg | Glu | Asn | Ala | Ile | Asp | Gly | Glu | His |
| | | | | 245 | | | | | 250 | | | | | 255 | |
| Ser | Gly | Lys | Ala | Thr | His | Ala | Arg | Ile | Gly | Gln | Ile | Cys | Lys | Asn | Asp |
| | | | | 260 | | | | | 265 | | | | | 270 | |
| Phe | Gly | Gly | His | Arg | Ser | Leu | Val | Asn | Lys | Trp | Thr | Thr | Phe | Leu | Lys |
| | | | | 275 | | | | | 280 | | | | | 285 | |
| Ala | Arg | Leu | Ile | Cys | Ser | Val | Pro | Gly | Pro | Asn | Gly | Ile | Asp | Thr | His |
| | | 290 | | | | | 295 | | | | | 300 | | | |
| Phe | Asp | Glu | Leu | Gln | Asp | Val | Phe | Leu | Met | Asn | Phe | Lys | Asp | Pro | Lys |
| 305 | | | | | 310 | | | | | 315 | | | | | 320 |
| Asn | Pro | Val | Val | Tyr | Gly | Val | Phe | Thr | Thr | Ser | Ser | Asn | Ile | Phe | Lys |
| | | | | 325 | | | | | 330 | | | | | 335 | |
| Gly | Ser | Ala | Val | Cys | Met | Tyr | Ser | Met | Ser | Asp | Val | Arg | Arg | Val | Phe |
| | | | | 340 | | | | | 345 | | | | | 350 | |
| Leu | Gly | Pro | Tyr | Ala | His | Arg | Asp | Gly | Pro | Asn | Tyr | Gln | Trp | Val | Pro |
| | | | | 355 | | | | | 360 | | | | | 365 | |

-continued

```
Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
                420                 425                 430

Gln Ile Val Val Asp Arg Val Asp Ala Glu Asp Gly Gln Tyr Asp Val
            435                 440                 445

Met Phe Ile Gly Thr Asp Val Gly Thr Val Leu Lys Val Val Ser Ile
450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
                500                 505                 510

Pro Leu His Arg Cys Asp Ile Tyr Gly Lys Ala Cys Ala Glu Cys Cys
                515                 520                 525

Leu Ala Arg Asp Pro Tyr Cys Ala Trp Asp Gly Ser Ala Cys Ser Arg
530                 535                 540

Tyr Phe Pro Thr Ala Lys Arg Arg Thr Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Glu Arg Ile Ile Tyr Gly Val Glu Asn Ser Ser
                580                 585                 590

Thr Phe Leu Glu Cys Ser Pro Lys Ser Gln Arg Ala Leu Val Tyr Trp
                595                 600                 605

Gln Phe Gln Arg Arg Asn Glu Glu Arg Lys Glu Glu Ile Arg Val Asp
                610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
                645                 650                 655

Ile Gln Thr Leu Leu Lys Val Thr Leu Glu Val Ile Asp Thr Glu His
                660                 665                 670

Leu Glu Glu Leu Leu His Lys Asp Asp Gly Asp Gly Ser Lys Thr
                675                 680                 685

Lys Glu Met Ser Asn Ser Met Thr Pro Ser Gln Lys Val Trp Tyr Arg
                690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
                725                 730                 735

Pro Gly His Thr Pro Gly Asn Ser Asn Lys Trp Lys His Leu Gln Glu
                740                 745                 750

Asn Lys Lys Gly Arg Asn Arg Arg Thr His Glu Phe Glu Arg Ala Pro
                755                 760                 765

Arg Ser Val
    770
```

<210> SEQ ID NO 2
<211> LENGTH: 2316
<212> TYPE: DNA
<213> ORGANISM: Artificial Sequence
<220> FEATURE:
<223> OTHER INFORMATION: cDNA

<400> SEQUENCE: 2

```
atgggctggt taactaggat tgtctgtctt ttctggggag tattacttac agcaagagca      60
aactatcaga tgggaagaa  caatgtgcca aggctgaaat tatcctacaa agaaatgttg     120
gaatccaaca atgtgatcac tttcaatggc ttggccaaca gctccagtta tcataccttc     180
cttttggatg aggaacggag taggctgtat gttggagcaa aggatcacat attttcattc     240
gacctggtta atatcaagga ttttcaaaag attgtgtggc cagtatctta caccagaaga     300
gatgaatgca gtgggctgg  aaaagacatc ctgaaagaat gtgctaattt catcaaggta     360
cttaaggcat ataatcagac tcacttgtac gcctgtggaa cggggggcttt tcatccaatt     420
tgcacctaca ttgaaattgg acatcatcct gaggacaata ttttaagct  ggagaactca     480
cattttgaaa acggccgtgg gaagagtcca tatgacccta gctgctgac  agcatccctt     540
ttaatagatg agaattata  ctctggaact gcagctgatt tatgggggcg agactttgct     600
atcttccgaa ctcttgggca ccaccaccca atcaggacag agcagcatga ttccaggtgg     660
ctcaatgatc caaagttcat tagtgcccac ctcatctcag agagtgacaa tcctgaagat     720
gacaaagtat acttttttctt ccgtgaaaat gcaatagatg gagaacactc tggaaaagct     780
actcacgcta aataggtca  gatatgcaag aatgactttg gagggcacag aagtctggtg     840
aataaatgga caacattcct caaagctcgt ctgatttgct cagtgccagg tccaaatggc     900
attgacactc attttgatga actgcaggat gtattcctaa tgaactttaa agatcctaaa     960
aatccagttg tatatggagt gtttacgact tccagtaaca ttttcaaggg atcagccgtg    1020
tgtatgtata gcatgagtga tgtgagaagg gtgttccttg gtccatatgc ccacagggat    1080
ggacccaact atcaatgggt gccttatcaa ggaagagtcc cctatccacg gccaggaact    1140
tgtcccagca aaacatttgg tggttttgac tctacaaagg accttcctga tgatgttata    1200
acctttgcaa gaagtcatcc agccatgtac aatccagtgt ttcctatgaa caatcgccca    1260
atagtgatca aaacggatgt aaattatcaa tttacacaaa ttgtcgtaga ccgagtggat    1320
gcagaagatg gacagtatga tgttatgttt atcggaacag atgttgggac cgttcttaaa    1380
gtagtttcaa ttcctaagga gacttggtat gatttagaag aggttctgct ggaagaaatg    1440
acagttttc  gggaaccgac tgctatttca gcaatggagc tttccactaa gcagcaacaa    1500
ctatatattg gttcaacggc tgggggttgcc cagctcccctt tacaccggtg tgatatttac    1560
gggaaagcgt gtgctgagtg ttgcctcgcc cgagacccctt actgtgcttg ggatggttct    1620
gcatgttctc gctatttcc  cactgcaaag agacgcacaa gacgacaaga tataagaaat    1680
ggagacccac tgactcactg ttcagactta caccatgata tcaccatgg  ccacagccct    1740
gaagagagaa tcatctatgg tgtagagaat agtagcacat ttttggaatg cagtccgaag    1800
tcgcagagag cgctggtcta ttggcaattc cagaggcgaa atgaagagcg aaaagaagag    1860
atcagagtgg atgatcatat catcaggaca gatcaaggcc ttctgctacg tagtctacaa    1920
cagaaggatt caggcaatta cctctgccat gcggtggaaa catgggttcat acaaactctt    1980
cttaaggtaa ccctggaagt cattgacaca gagcatttgg aagaacttct tcataaagat    2040
gatgatggag atggctctaa gaccaaagaa atgtccaata gcatgacacc tagccagaag    2100
```

-continued

```
gtctggtaca gagacttcat gcagctcatc aaccacccca atctcaacac aatggatgag    2160
ttctgtgaac aagtttggaa aagggaccga aaacaacgtc ggcaaaggcc aggacatacc    2220
ccagggaaca gtaacaaatg gaagcactta caagaaaata agaaggtag  aaacaggagg    2280 acccacgaat tgagagggc  acccaggagt gtctga                              2316
```

<210> SEQ ID NO 3
<211> LENGTH: 779
<212> TYPE: PRT
<213> ORGANISM: Artificial Sequence
<220> FEATURE:
<223> OTHER INFORMATION: Synthetic polypeptide

<400> SEQUENCE: 3

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320
```

```
Asn Pro Val Val Tyr Gly Val Phe Thr Thr Ser Ser Asn Ile Phe Lys
            325                 330                 335

Gly Ser Ala Val Cys Met Tyr Ser Met Ser Asp Val Arg Arg Val Phe
        340                 345                 350

Leu Gly Pro Tyr Ala His Arg Asp Gly Pro Asn Tyr Gln Trp Val Pro
        355                 360                 365

Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
            405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
        435                 440                 445

Met Phe Ile Gly Thr Asp Val Gly Thr Val Leu Lys Val Val Ser Ile
    450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
            485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ala Cys Ser Arg
    530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His His Asp Asn His His
            565                 570                 575

Gly His Ser Pro Glu Glu Arg Ile Ile Tyr Gly Val Glu Asn Ser Ser
            580                 585                 590

Thr Phe Leu Glu Cys Ser Pro Lys Ser Gln Arg Ala Leu Val Tyr Trp
        595                 600                 605

Gln Phe Gln Arg Arg Asn Glu Glu Arg Lys Glu Glu Ile Arg Val Asp
    610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
            660                 665                 670

Leu Glu Glu Leu Leu His Lys Asp Asp Asp Gly Asp Gly Ser Lys Thr
        675                 680                 685

Lys Glu Met Ser Asn Ser Met Thr Pro Ser Gln Lys Val Trp Tyr Arg
    690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
            725                 730                 735
```

```
Pro Gly His Thr Pro Gly Asn Ser Asn Lys Trp Lys His Leu Gln Glu
            740             745             750

Asn Lys Lys Gly Arg Asn Arg Arg Thr His Glu Phe Glu Arg Ala Pro
        755             760             765

Arg Ser Val Asp Tyr Lys Asp Asp Asp Lys
    770             775
```